(12) United States Patent
Heacock et al.

(10) Patent No.: US 7,288,106 B2
(45) Date of Patent: Oct. 30, 2007

(54) SYSTEM AND METHOD FOR EXCITATION OF PHOTOREACTIVE COMPOUNDS IN EYE TISSUE

(75) Inventors: Gregory L. Heacock, Auburn, WA (US); Darrin Huston, Enumclaw, WA (US); James C. Chen, Bellevue, WA (US); Steven R. Daly, Sammamish, WA (US)

(73) Assignee: Light Sciences Oncology, Inc., Snoqualmie, WA (US)

( * ) Notice: Subject to any disclaimer, the term of this patent is extended or adjusted under 35 U.S.C. 154(b) by 426 days.

(21) Appl. No.: 10/677,645

(22) Filed: Oct. 2, 2003
(Under 37 CFR 1.47)

(65) Prior Publication Data

US 2004/0243198 A1    Dec. 2, 2004

Related U.S. Application Data

(60) Provisional application No. 60/415,948, filed on Oct. 3, 2002.

(51) Int. Cl.
*A61N 5/06* (2006.01)
(52) U.S. Cl. ............................................ 607/88; 606/4
(58) Field of Classification Search ................ 606/4–6; 607/88–94
See application file for complete search history.

(56) References Cited

U.S. PATENT DOCUMENTS

| | | | |
|---|---|---|---|
| 4,728,183 A | 3/1988 | Heacock et al. | |
| 4,951,663 A | 8/1990 | L'Esperance, Jr. | |
| 4,988,183 A | 1/1991 | Kasahara et al. | |
| 5,119,814 A | 6/1992 | Minnich | |
| 5,270,748 A | 12/1993 | Katz | |
| 5,336,215 A * | 8/1994 | Hsueh et al. | 606/4 |
| 5,530,495 A | 6/1996 | Lamprecht | |
| 5,609,159 A | 3/1997 | Kandel et al. | |
| 5,673,096 A * | 9/1997 | Dorsel et al. | 351/211 |
| 5,705,518 A | 1/1998 | Richter et al. | |
| 5,756,541 A | 5/1998 | Strong et al. | |
| 5,770,619 A | 6/1998 | Richter et al. | |
| 5,798,349 A | 8/1998 | Levy et al. | |
| 5,815,240 A | 9/1998 | Iki | |

(Continued)

FOREIGN PATENT DOCUMENTS

| | | |
|---|---|---|
| WO | WO 95/24930 | 9/1995 |
| WO | WO 01/51087 A2 | 7/2001 |
| WO | WO 01/58240 A2 | 8/2001 |
| WO | WO 01/74389 A2 | 10/2001 |

*Primary Examiner*—Henry M. Johnson, III
(74) *Attorney, Agent, or Firm*—McAndrews, Held & Malloy, Ltd.

(57) ABSTRACT

A system and method for excitation of photosensitizers is configured to provide desired illumination on targeted eye tissue. The excitation system includes an optical module that generates illumination and a controller to power the optical module and control the shape, intensity or energy level, and duration of the illumination. The optical module includes a contact portion for interfacing with the eye, a treatment beam portion including a light emitter array to generate shaped light patterns and optics to focus the light patterns onto the eye, and a visualization portion to provide visual feedback of treatment through a visualization interface coupled with a microscope. A typical treatment involves the optical module being placed on a diseased eye of a patient by a clinician to project illumination on a diseased portion of the eye. The clinician typically views the eye through the microscope and the optical module during treatment.

5 Claims, 19 Drawing Sheets

U.S. PATENT DOCUMENTS

| | | |
|---|---|---|
| 5,910,510 A | 6/1999 | Strong et al. |
| 5,935,076 A * | 8/1999 | Smith et al. ................ 600/479 |
| 5,956,124 A | 9/1999 | Dan |
| 5,997,141 A | 12/1999 | Heacock |
| 6,007,204 A | 12/1999 | Fahrenkrug et al. |
| 6,043,237 A | 3/2000 | Meadows et al. |
| 6,056,403 A | 5/2000 | Fisher et al. |
| 6,117,862 A | 9/2000 | Margaron et al. |
| 6,186,628 B1 | 2/2001 | Van de Velde |
| 6,214,819 B1 | 4/2001 | Brazzell et al. |
| RE37,180 E | 5/2001 | Mori et al. |
| 6,225,303 B1 | 5/2001 | Miller et al. |
| 6,297,228 B1 | 10/2001 | Clark |
| 6,319,273 B1 | 11/2001 | Chen et al. |
| 6,319,274 B1 | 11/2001 | Shadduck |
| 6,333,988 B1 * | 12/2001 | Seal et al. ................ 382/117 |
| 6,471,691 B1 | 10/2002 | Kobayashi et al. |
| 6,494,878 B1 * | 12/2002 | Pawlowski et al. ............ 606/4 |
| 2001/0039438 A1 | 11/2001 | Brazzell |
| 2002/0122572 A1 * | 9/2002 | Seal et al. ................ 382/117 |
| 2002/0165525 A1 | 11/2002 | Nakamura |
| 2003/0009155 A1 | 1/2003 | Pawlowski et al. |
| 2003/0009205 A1 | 1/2003 | Biel |
| 2003/0025877 A1 | 2/2003 | Yancey et al. |
| 2003/0109907 A1 | 6/2003 | Shadduck |
| 2003/0189690 A1 | 10/2003 | Mihashi et al. |
| 2003/0193647 A1 | 10/2003 | Neal et al. |
| 2003/0223039 A1 | 12/2003 | Thomas |
| 2003/0231285 A1 | 12/2003 | Ferguson |
| 2004/0002694 A1 | 1/2004 | Pawlowski et al. |

* cited by examiner

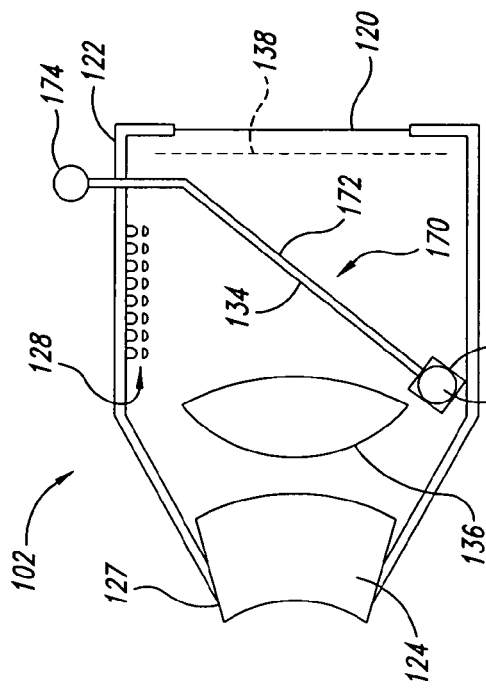
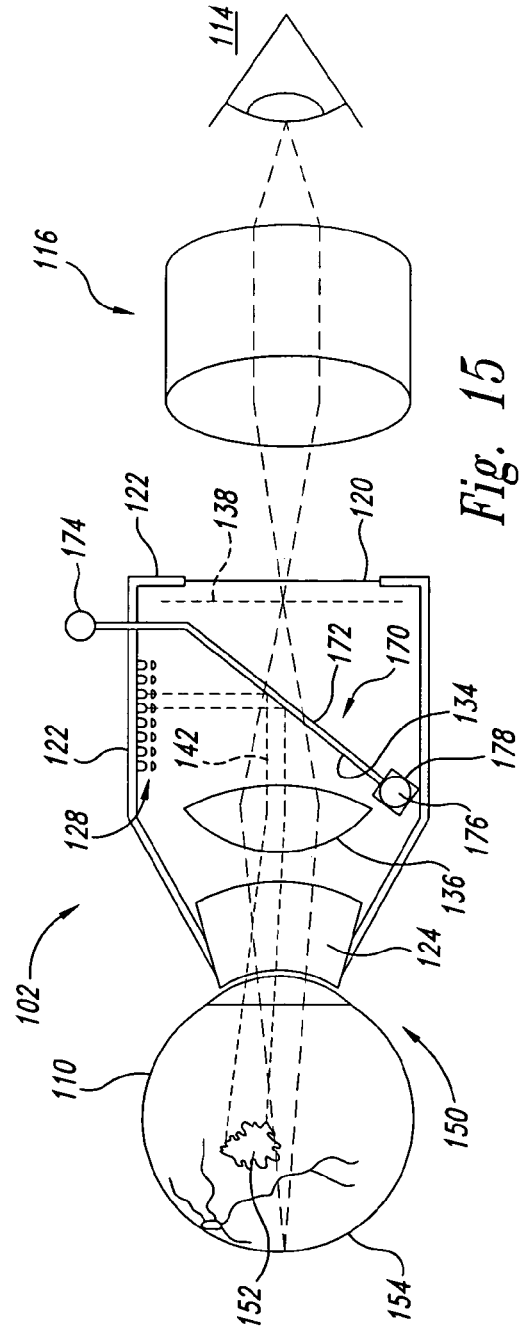

SYSTEM AND METHOD FOR EXCITATION OF PHOTOREACTIVE COMPOUNDS IN EYE TISSUE

CROSS-REFERENCE TO RELATED APPLICATION

This application claims the benefit of U.S. Provisional Patent Application No. 60/415,948, filed Oct. 3, 2002, which is incorporated herein by reference in its entirety.

BACKGROUND OF THE INVENTION

1. Field of the Invention

The invention relates, in general, to treatment of ocular disease, and, in particular, to systems and methods for excitation of photoreactive compounds in eye tissue.

2. Description of the Related Art

Diseased cells may be killed by triggering a class of photoreactive compounds or photosensitizers with specific illumination wavelengths. Photosensitizers are used in photodynamic therapy (PDT) through light sources such as lasers to treat targeted eye tissue in a number of eye disease conditions. For example, in age related macular degeneration (AMD), glaucoma, and diabetic retinopathy (DR), photosensitizers may be used to inhibit formation or retard disease progression such as commonly indicated by sub-retinal fluid concentration, or rapidly uncontrolled vascular growth within diseased eye tissue. As an example, diseased eye tissue 10 can occur on a rear portion 12 of an eye 14, as shown in FIG. 1. The diseased eye tissue 10 would be a candidate for being targeted eye tissue in PDT.

Retardation or termination of uncontrolled vessel growth provides promise of extended visual function. Conventional approaches to PDT are challenged by requirements of light exposure of desired intensities, duration, shape, and timing when photosensitizers are present in the diseased tissue. Unfortunately, inaccurately generated illumination, such as misdirected or misshaped illumination, could cause photosensitizers to kill healthy eye tissue.

BRIEF SUMMARY OF THE INVENTION

The present invention resides in a method and system for excitation of photoreactive compounds in eye tissue. Embodiments include a system for illuminating a target area of an eye treated with a photosensitizer. The system includes a contact portion configured to interface with the eye to provide an optical path between the eye and the system. A plurality of light emitters are configured to emit light having an emissions spectrum with at least an activation wavelength of the photosensitizer. A selective reflector is configured to reflect at least a majority of light having the activation wavelength of the photosensitizer and to pass at least some light having wavelengths other than the activation wavelength. The selective reflector is positioned to receive emitter light and to direct a portion of the emitter light reflected from the selective reflector toward the contact portion. The selective reflector is further positioned to receive and pass a portion of light reflected from the eye and passed by the contact portion. A visualization portion is positioned to receive and pass that portion of light reflected from the eye and passed by the selective reflector.

Some embodiments include a computer linked to the light emitters, the computer configured to display input controls for selection of which light emitters to activate. Some embodiments include a controller configured to control intensity of the emitter light from the light emitters between at least two levels: a treatment level having an intensity level sufficient to activate the photosensitizer and a targeting level having an intensity level insufficient to activate the photosensitizer. Some embodiments include a lens positioned between the selective reflector and the contact portion, the lens shaped to direct, at least in part, reflected emitter light toward the target area of the eye, the lens further shaped to direct, at least in part, a portion of the light reflected from the eye to be passed by the selective reflector onto an image plane, the selective reflector being located between the lens and the image plane. Some embodiments include a lens positioned between the plurality of light emitters and the selective reflector, the lens shaped to direct, at least in part, emitter light to be reflected off of the selective reflector toward the target area of the eye. Some embodiments include a computer linked to the light emitters, the computer configured to display input controls for selection of duration and intensity of the emitter light. Some embodiments include an electronic image capture device positioned to receive as an image a portion of the light passed by the selective reflector.

Some embodiments include a controller electrically coupled to the plurality of light emitters to selectively activate ones of the light emitters; an electronic monitor electrically coupled to the electronic image capture device to display images captured by the electronic image capture device; and a touch screen device overlayed onto the electronic monitor, the touch screen device electrically coupled to the controller to select activation of the light emitters. Some embodiments include a computer linked to the light emitters, the computer configured to display input controls for selection of which light emitters to activate. Some embodiments include a selective reflector positioned to receive emitter light and to direct a portion of the emitter light toward the contact portion, the plurality of light emitters movably mounted such that position of the plurality of light emitters with respect to the selective reflector is adjustable.

Some embodiments include a method for illuminating a target area of an eye, wherein the method includes emitting light having an emissions spectrum with at least an activation wavelength of a photosensitizer; and simultaneously reflecting a portion of the emitted light toward the target area of the eye and passing at least a portion of light that had been reflected off of the eye for observation of the eye. Some embodiments include a method for illuminating a target area of an eye, the target area having a shape, wherein the method includes selecting from a plurality of light emitters, ones of the emitters to activate based upon the shape of the target area; emitting light from the selected emitters; simultaneously reflecting a portion of the emitted light from the selected emitters and directing the reflected light toward the target area of the eye and passing a portion of light that had been reflected off of the eye; and using at least a portion of light reflected off of the eye that has been passed to observe the eye. Some embodiments include aligning the reflected emitted light with the target area.

Other features and advantages of the invention will become apparent from the following detailed description, taken in conjunction with the accompanying drawings.

BRIEF DESCRIPTION OF THE SEVERAL VIEWS OF THE DRAWING(S)

FIG. 14 is a cross-sectional schematic of another implementation of the optical module.

FIG. 15 is a cross-sectional schematic showing an optical raytrace with the optical module shown in FIG. 14.

DETAILED DESCRIPTION OF THE INVENTION

Figure 1:
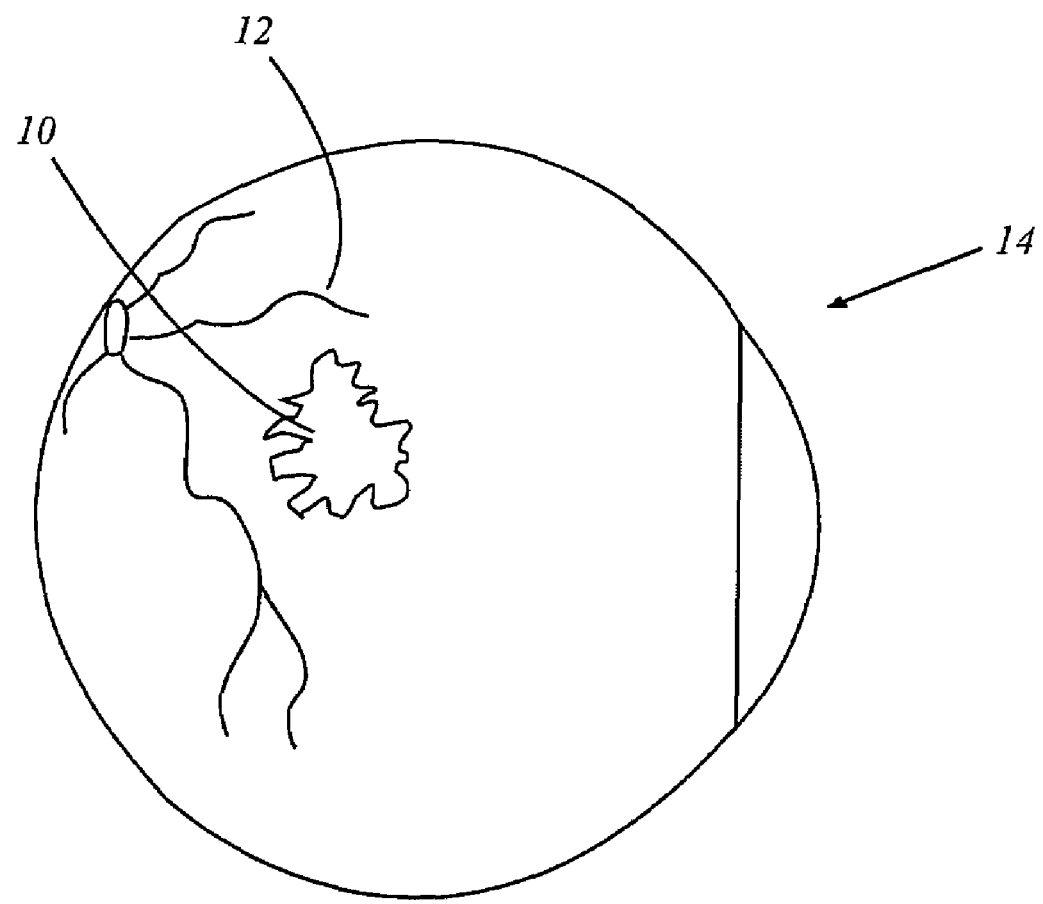
FIG. 1 is an illustration of an eye with a diseased portion.
Figure 2:
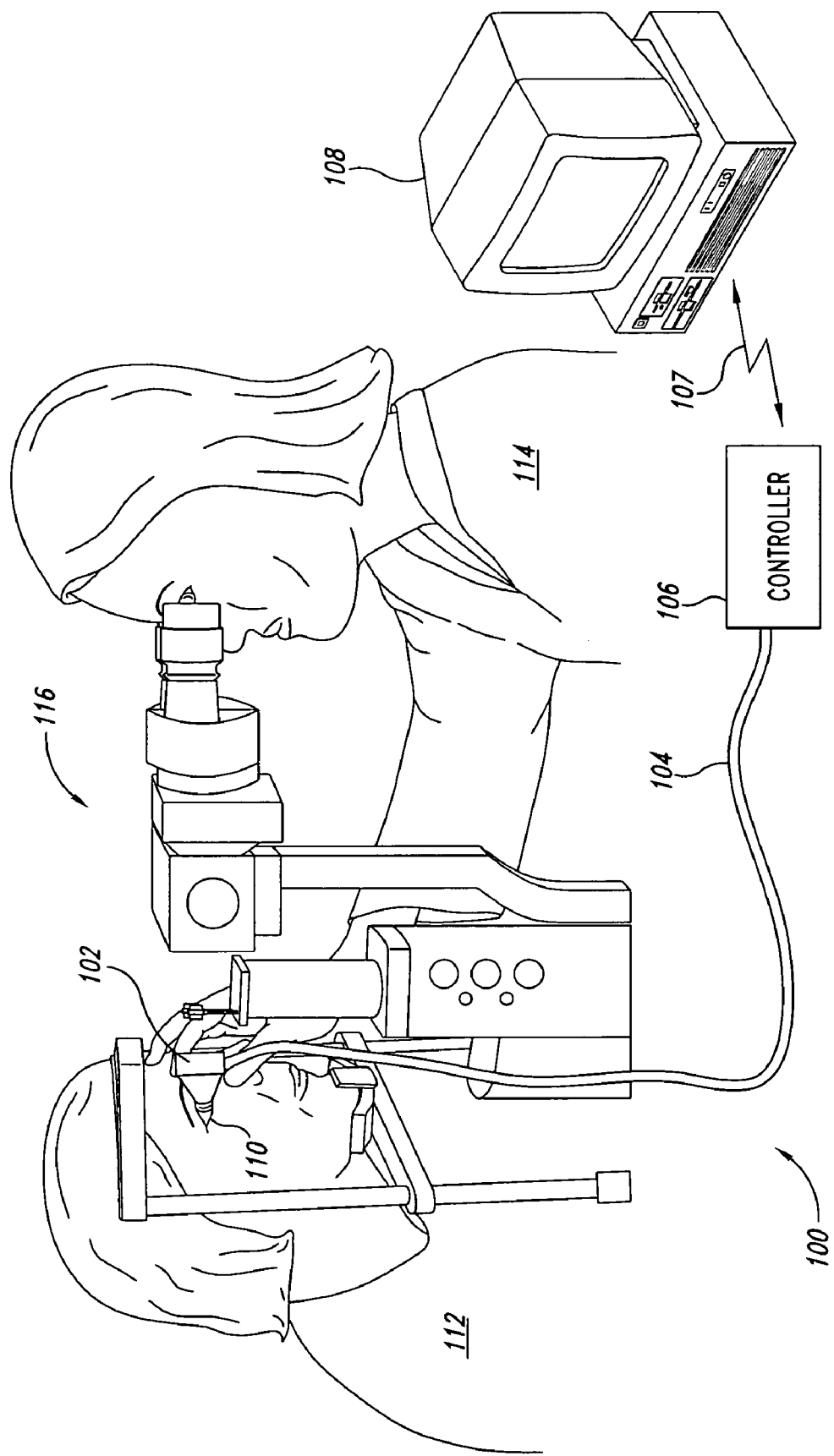
FIG. 2 is a schematic illustrating a use by a physician of a system for excitation of photosensitizers in eye tissue of a patient such as the diseased portion of the representative eye shown in FIG. 1.

A system and method for excitation of photosensitizers in eye tissue is described herein to provide desired illumination on targeted eye tissue. The excitation system generally includes an optical module that generates illumination and a controller to power the optical module and control the shape, intensity or energy level, and duration of the illumination. An implementation is shown in FIG. 2 as an excitation system 100 that includes an optical module 102 for generation of treatment illumination, communicatively linked, such as by a control line 104, to a controller 106 for modulating the shape to closely match that of targeted eye tissue, energy level, and duration of the treatment illumination. In some implementations, the controller 106 is communicatively linked, such as by a wireless link 107, to a workstation computer 108 used in set-up and operation of the treatments. A typical treatment procedure involves the optical module 102 being placed on a diseased eye 110 of a patient 112 by a clinician 114 to project illumination onto a diseased portion of the eye. The clinician 114 typically views the eye 110 through a microscope 116 and the optical module 102 during treatment.

In general, the optical module 102 includes a contact portion to interface the optical module to the diseased eye 110, a treatment beam portion, and a visualization portion. The treatment beam portion generally comprises a multitude of light emitters externally controlled to generate a desired pattern of therapeutic light and optical elements to assist in focusing the generated pattern onto targeted eye tissues. The visualization portion acts as an interface between external viewing devices, such as the microscope 116 or video camera, used by a doctor, such as the clinician 114, and the optical elements of the contact portion and treatment beam portion. The visualization portion allows the attending doctor to observe internal eye tissues and the therapeutic illumination light simultaneously.

Figure 3:
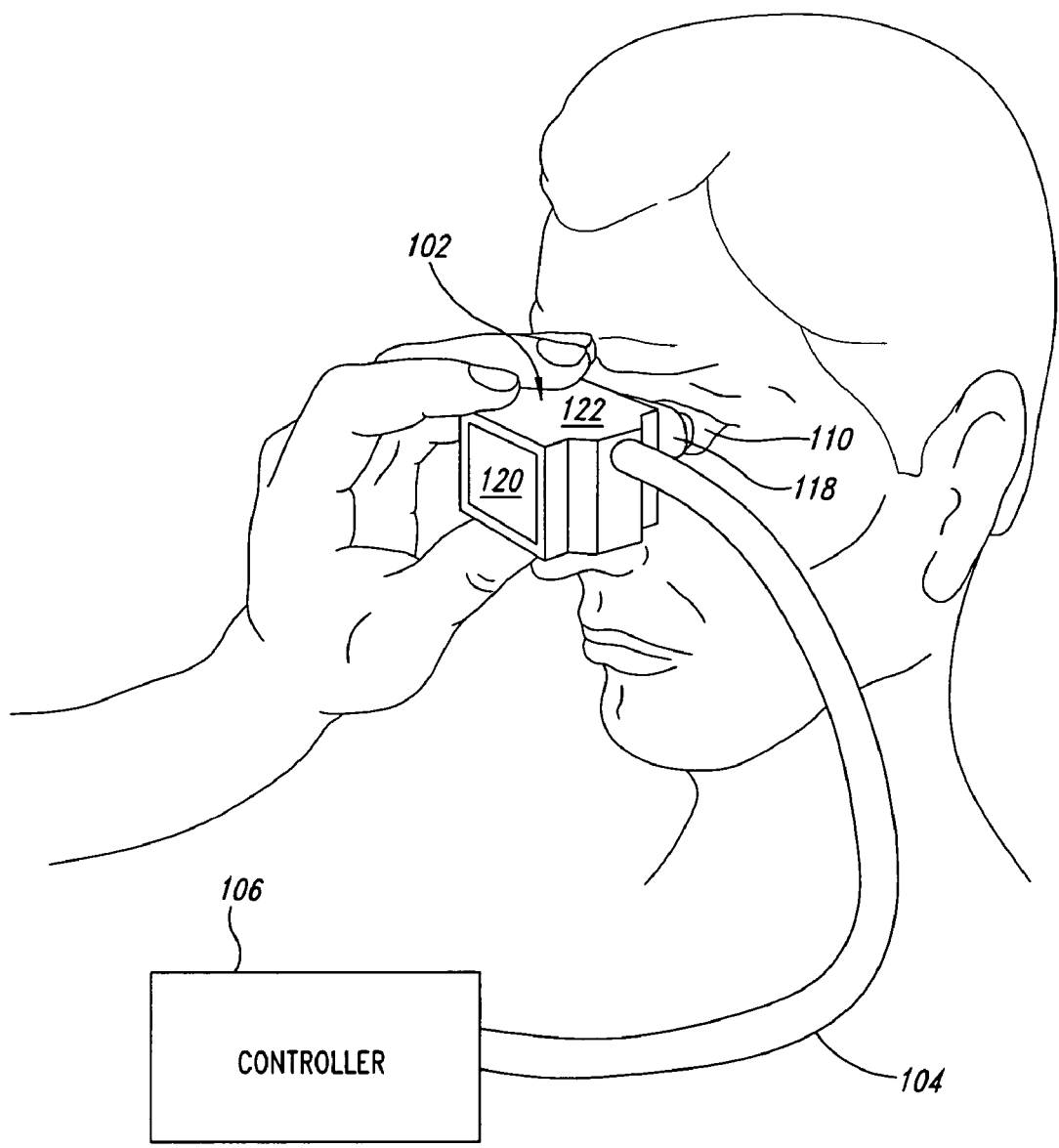
FIG. 3 is a schematic illustrating an optical module of the excitation system shown in FIG. 2.

An implementation of the optical module 102 shown in FIG. 3 includes a contact component 118 to be placed on the eye 110 of the patient 112 as an implementation of the contact portion, a visualization interface 120 as part of the visualization portion, and a housing 122 as shown in FIG. 3. The visualization interface 120 is typically either an optic lens or a viewing pane to allow the physician 114 to view the eye 110 by placing the microscope 116 near to the visualization interface 120. The housing 122 contains and holds an illumination source and optical components, such as a reflector, in rigid alignment.

Figure 4:
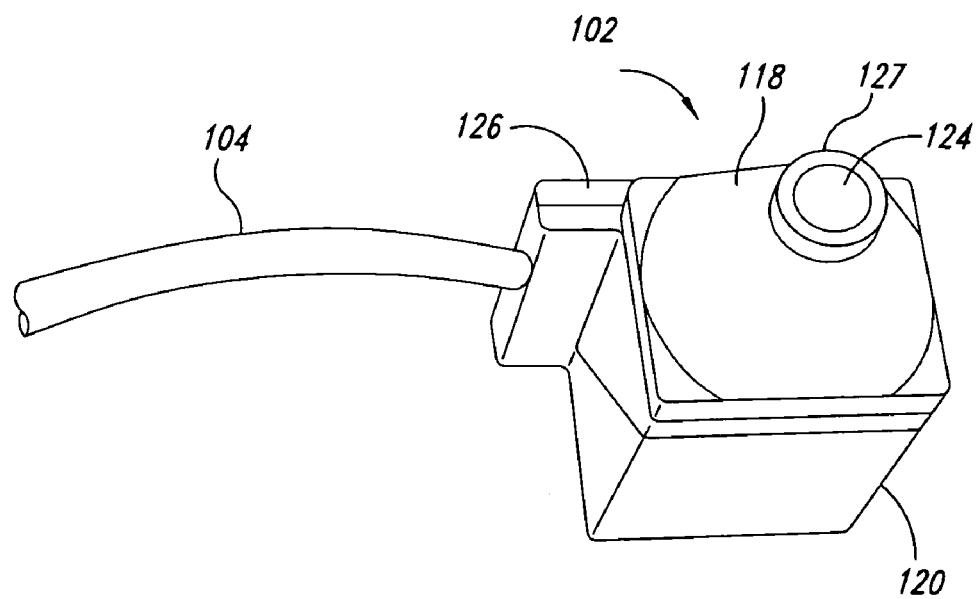
FIG. 4 is an illustration showing the contact element side of the optical module shown in FIG. 3 to be placed on an eye to be treated, such as an eye of the representative patient shown in FIG. 2.

The contact component 118 of the optical module 102 further includes a contact 124, as shown in FIG. 4, to be placed typically onto the cornea of the eye 110 of the patient 112 with use of a conventional interfacing eye gel. The contact 124 serves to neutralize the optical power of the cornea of the eye 110 so that treatment illumination may be directed to targeted eye tissue, such as the diseased eye portion 10. The housing 122 includes a protrusion 126 for steadying the contact 124 on the eye 110. The housing also includes a mount 127 that is rotatably coupled to the contact 124 to allow for aiming and manipulation by the clinician 114 of targeting strength illumination onto targeted eye tissue before treatment is begun using treatment strength illumination.

Figure 5:
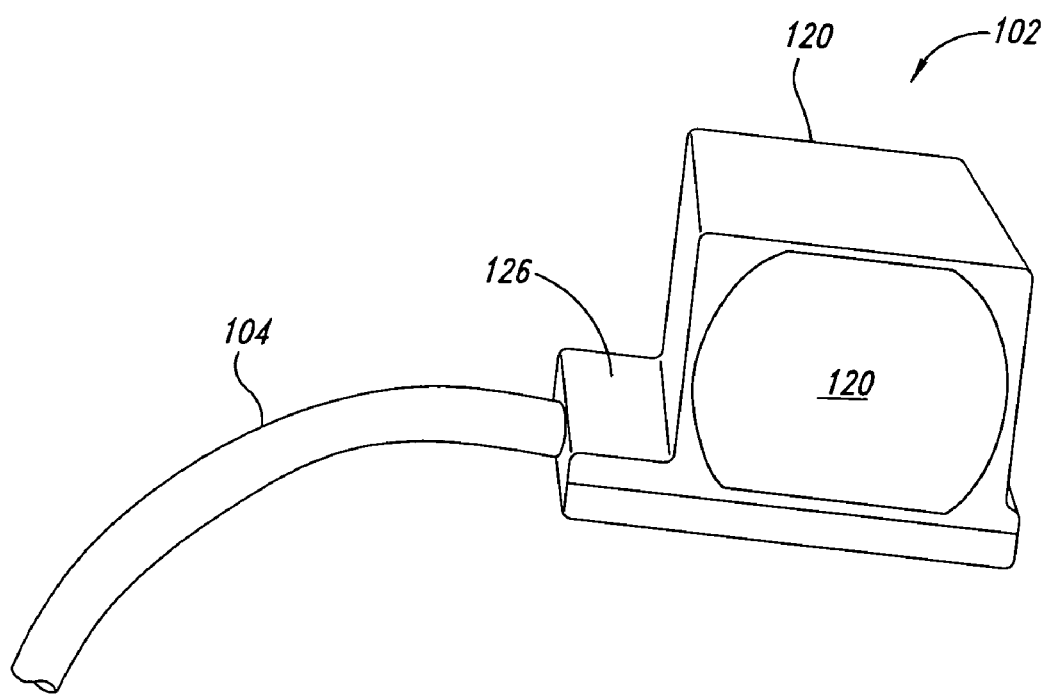
FIG. 5 is an illustration showing the visualization interface of the optical module shown in FIG. 3 to be typically viewed by a physician through a microscope such as shown in FIG. 2 to see a treated eye.
Figure 6:
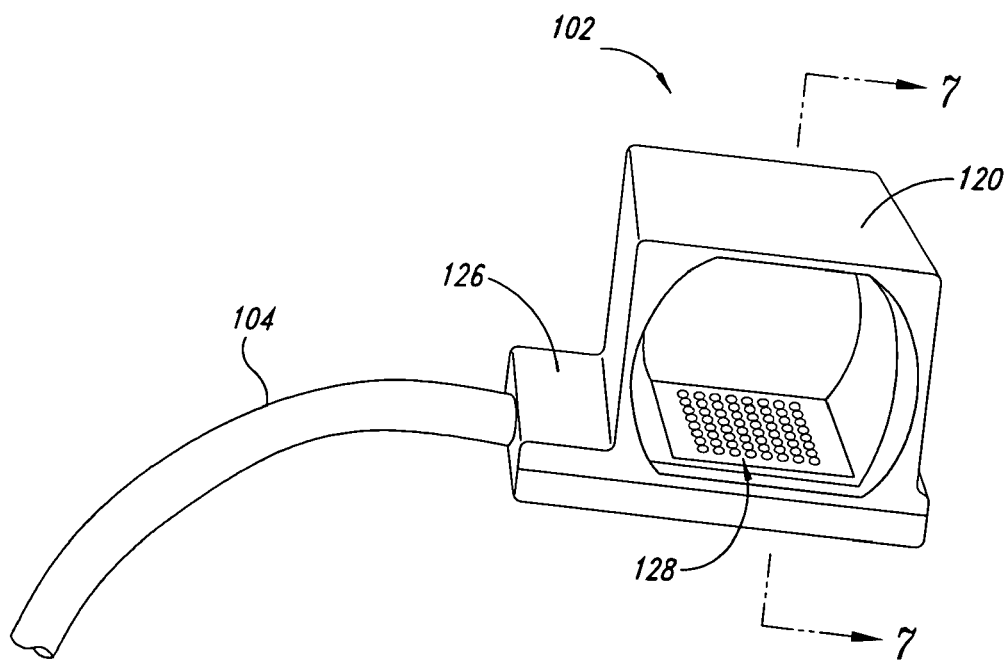
FIG. 6 is an illustration showing internal detail of the optical module shown in FIG. 3 as seen from the side shown in FIG. 5.

FIG. 5 shows a front view of the visualization interface 120 to be placed near the microscope 116 as shown in FIG. 2. FIG. 6 shows the same front view as FIG. 5 with the visualization interface 120 removed. An illumination source 128 is located inside of the housing 122 and includes a fully populated array of light emitting diodes (LEDs). Other implementations use back-illuminated liquid crystal displays, forward-illuminated reflective liquid crystal displays, a laser diode array, a coherent fiber bundle, an array of incandescent bulbs, an array of cold cathode fluorescent tubes, and/or an array of other light emitters. Other implementations, as further discussed below, use partially populated arrays. The exemplary implementation of the illumination source 128 as shown in FIG. 6 contains an 8×8 array of LEDs having a square shaped perimeter. Other implementations contain other configured arrays of various other numbers of LEDs forming other sized arrays having square or rectangularly shaped perimeters, such as a 16×16 array, or a 12×16 array. Other implementations use other arrangements of LEDs such as arrays of LEDs having circular or oval shaped perimeters or other symmetrically or non-symmetrically shaped perimeters.

Figure 7:
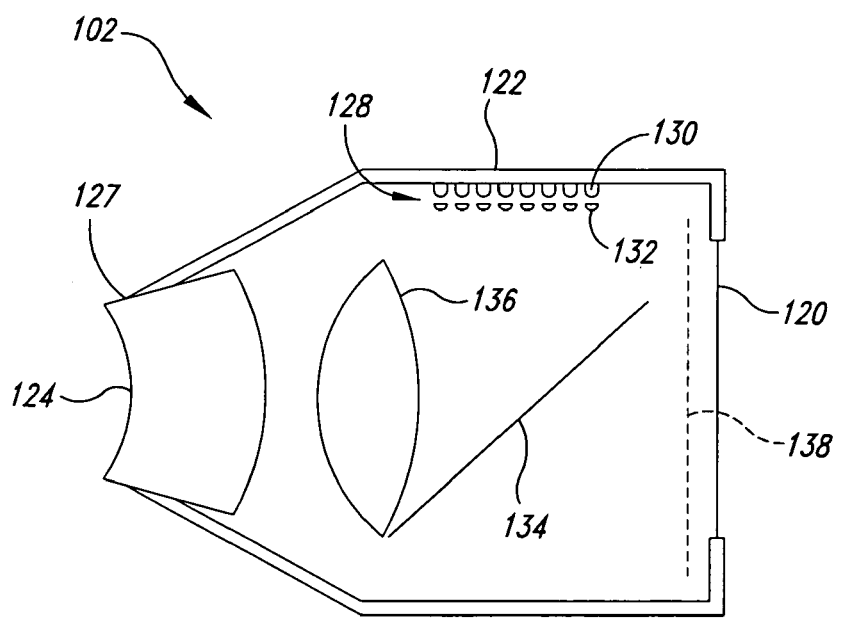
FIG. 7 is a cross-sectional schematic showing additional internal detail of the optical module shown in FIG. 6.
Figure 8:
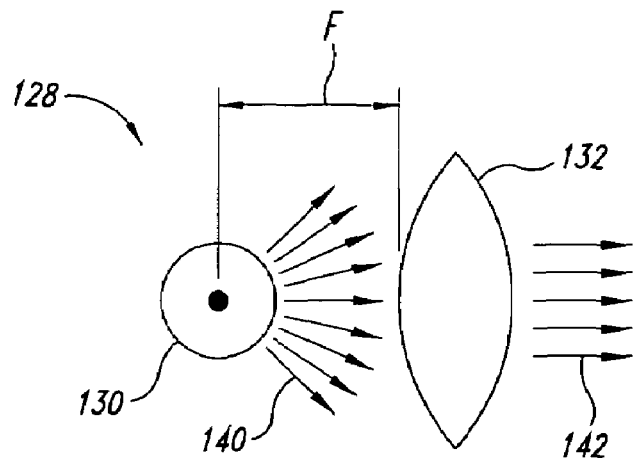
FIG. 8 is a schematic showing positioning of an LED of the optical module shown in FIG. 6 with respect to its lens.
Figure 9A:
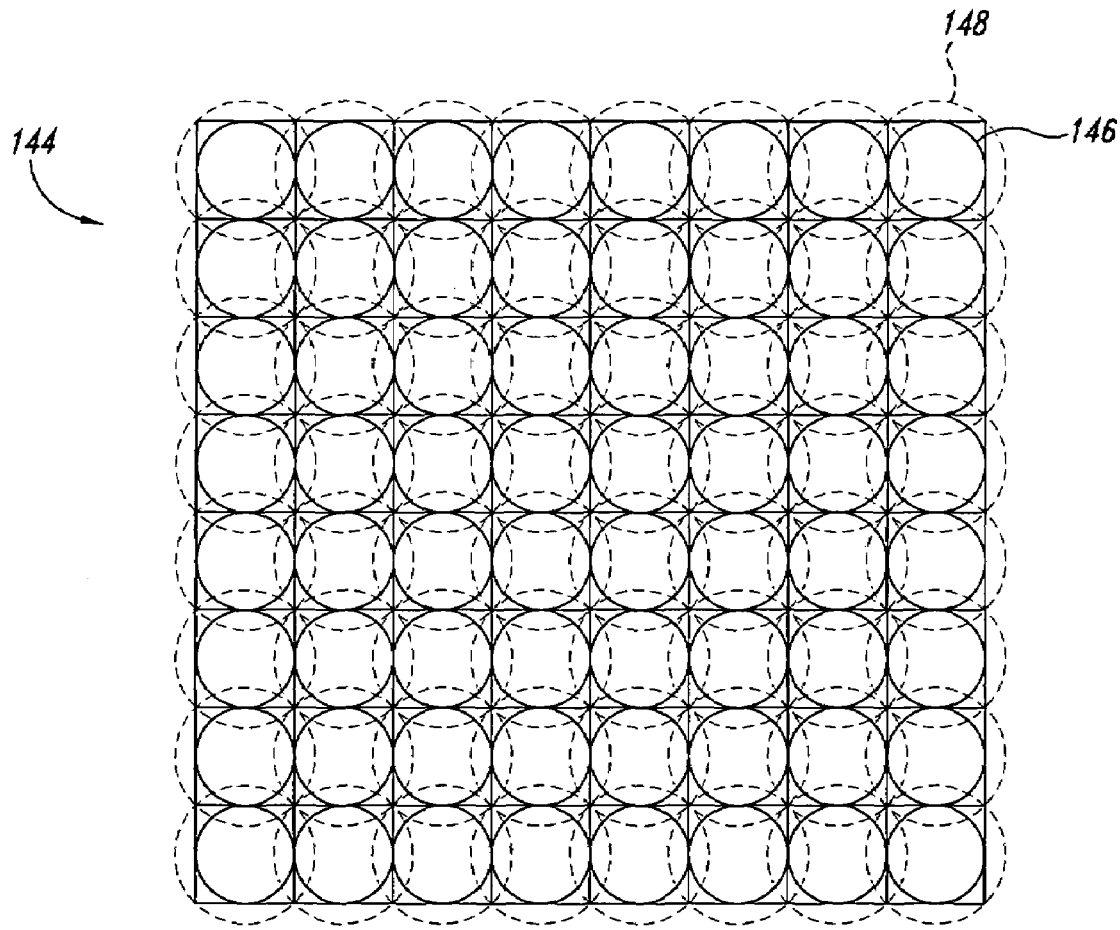
FIG. 9A is a schematic illustrating an illumination pattern resulting from an illumination source of the optical module shown in FIG. 6.
Figure 9B:
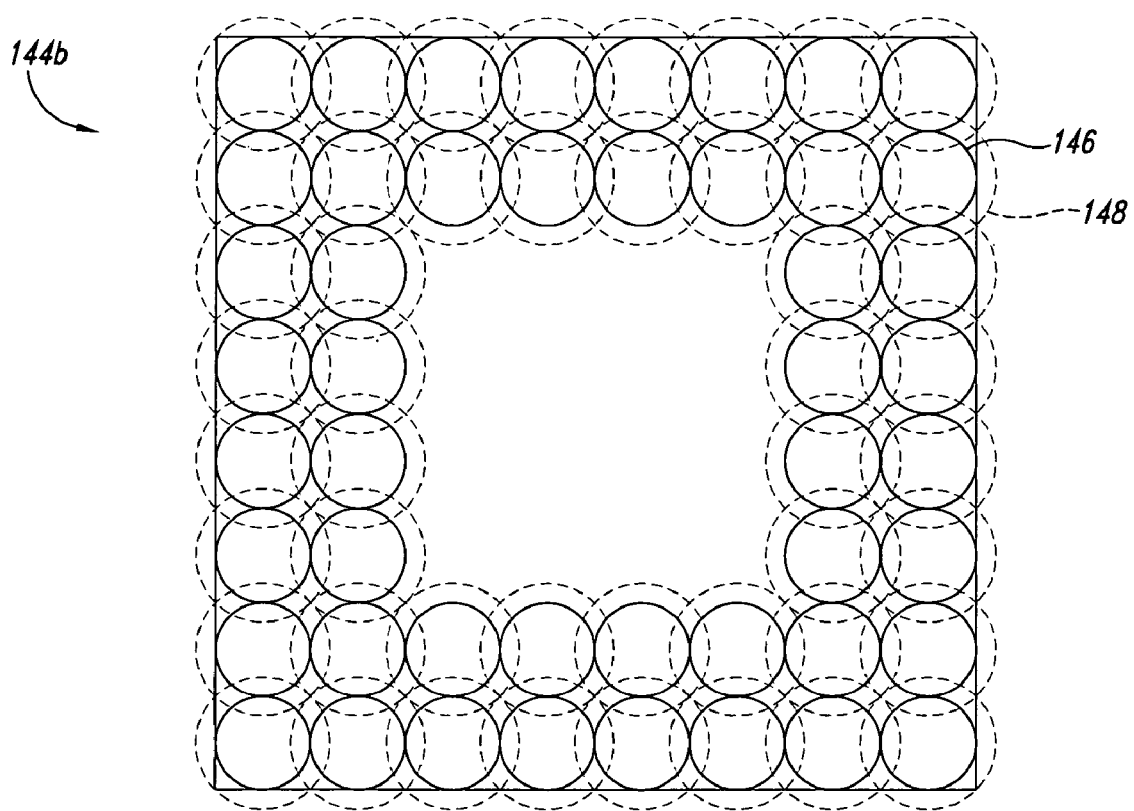
FIG. 9B is a schematic illustrating an alternative illumination pattern for treating disease such as DR.
Figure 9C:
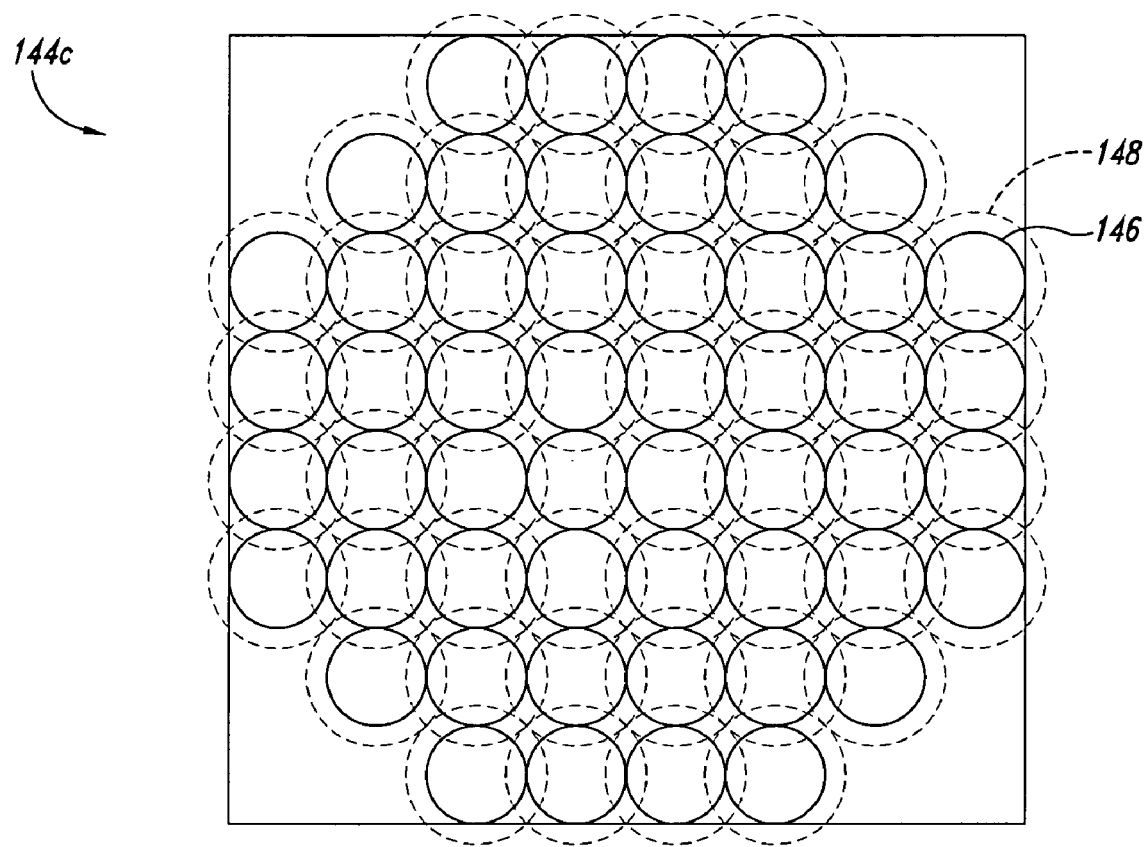
FIG. 9C is a schematic illustrating another alternative illumination pattern for treating disease such as glaucoma.

A cross sectional view, depicted in FIG. 7, of an implementation of the optical module 102 shows internal detail inside the housing 122. The illumination source 128 further includes a plurality of LEDs 130 configured to emit light upon activation and each with a complementary lens 132. As shown in FIG. 8, each complementary lens 132 is spaced from the correspondingly positioned LED 130 by approximately the focal length, F, of the complementary lens so that light 140 from the LED leaves the complementary lens as substantially parallel light 142. The LEDs 130 of the illumination source 128 are spaced from one another such that if all of the LEDs were turned on to illuminate a targeted eye tissue, a pattern 144, as shown in FIG. 9A, would result. For each of the LEDs 130, the pattern 144 has a primary excitation illumination area 146 and an overlap area 148 caused by Gaussian spread effects. Other implementations may use other type of spacing between the LEDs 130. Also, other configurations are used to produce alternative illumination patterns such as pattern 144b, shown in FIG. 9B, for treating disease such as DR and pattern 144c, shown in FIG. 9C, for treating other disease such as glaucoma wherein these illumination patterns are generated by partially populated arrays of emitters to, for instance, create peripheral coverage.

Figure 10:
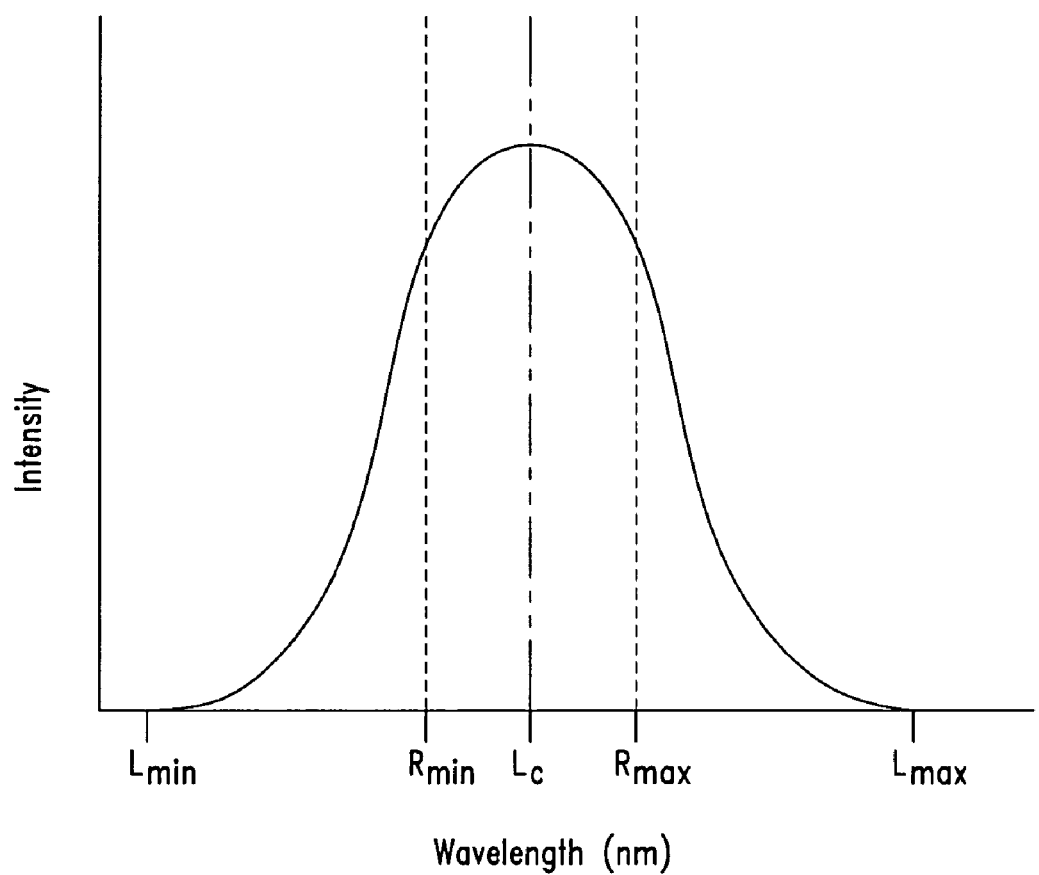
FIG. 10 is a graph showing an exemplary intensity distribution of the LED shown in FIG. 8.

Exemplary implementations of the LEDs 130 include emission spectra generally depicted in FIG. 10 as having a substantially Gaussian distribution of intensities across a particular range of wavelengths (e.g. $L_{min}$ to $L_{max}$) and having a center wavelength, $L_c$. A selective reflector 134 [see FIG. 7] is chosen to substantially reflect a particular spectrum (e.g. $R_{min}$ to $R_{max}$), known as a reflection spectrum, within the LED emission spectrum and to substantially pass other light outside the reflection spectrum, known as a pass spectrum, including that portion of the LED emission spectrum having wavelengths from $L_{min}$ to $R_{min}$ and $R_{max}$ to $L_{max}$. The photosensitizers are typically triggered by activation light having one or more particular activation wavelengths.

In general, photosensitizers are chemical compounds which home to one or more types of selected target cells and, when contacted by radiation, absorbs the light, which results in impairment or destruction of the target cells. Virtually any chemical compound that homes to a selected target and absorbs light may be used. In some implementations, the chemical compound is non-toxic to the subject to which it is administered or is capable of being formulated in a non-toxic composition. In further implementations, the chemical compound in its photo-degraded form is also non-toxic. An exemplary listing of photosensitizers may be found in Kreimer-Birnbaum, Sem. Hematol. 26:157-73, 1989. Photosensitizers include, but are not limited to, chlorins, alkyl ether analogs of chlorins, bacteriochlorophllys, bacteriochlorophlly derivatives, phthalocyanines, porphyrins, purpurins, merocyanines, psoralens, benzoporphyrin derivatives (BPD) and porfimer sodium and pro-drugs such as δ-aminolevulinic acid, which can produce drugs such as protoporphyrin. Other compounds include indocyanine green (ICG); methylene blue; toluidine blue; texaphyrins; and any other agent that absorbs light in a range of 500 nm-1100 nm. Other photosensitizers include LS 11, having an activation wavelength of approximately 660±5 nm, which is also known as taporfin sodium, talaporfin sodium, MACE, ME2906, mono-l-aspartyl chlorin e6, and NPe6.

The emission spectrum of the LEDs 130 is so selected that the one or more activation wavelengths are typically included within the LED emission spectrum substantially near the center wavelength, $L_c$, of the LED emission spectrum. The selective reflector 134 is generally chosen to have gradations of reflection efficiency with high reflection efficiency (approximately 99% of incident light is reflected) at or near the activation wavelength of the selected photosensitizer and lower efficiencies (e.g. 80% of incident light is reflected) at or near $L_{min}$ and $L_{max}$. FIG. 10 depicts the reflection spectrum of the selective reflector 134 as having the minimum wavelength, $L_{min}$, and the maximum wavelength, $L_{max}$, equally spaced from the center wavelength, $L_c$, but other implementations can use unequal spacing of the minimum and maximum reflection spectrum wavelengths from the center reflection spectrum wavelength.

Also found inside the housing is a lens 136 that serves roles for both the treatment beam and visualization portions of the optical module 102. In its treatment beam role, the lens 136 focuses the light from the illumination source 128 onto targeted eye tissue. In its visualization role, the lens focuses light onto an image plane 138 so that the targeted eye tissue can be viewed through the microscope 116 by the clinician 114.

Figure 11A:
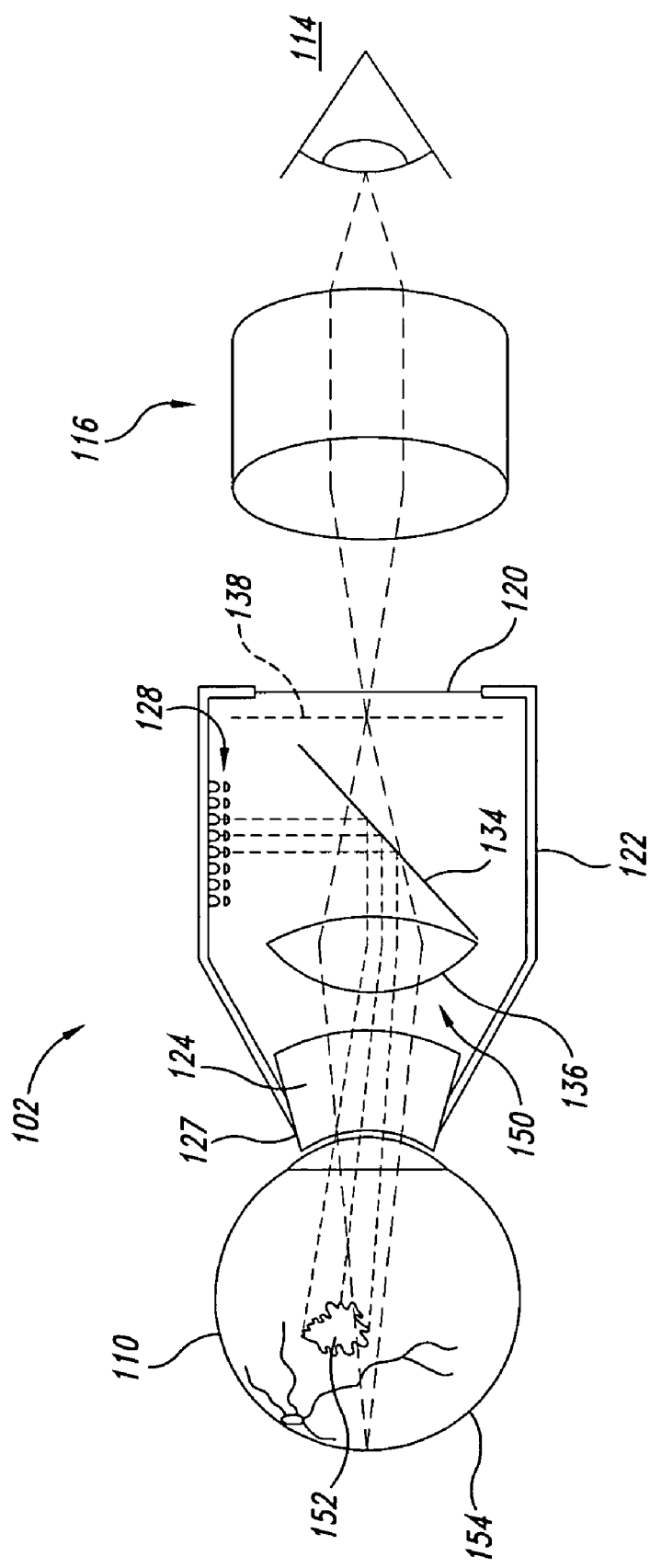
FIG. 11A is a cross-sectional schematic showing an optical raytrace of the optical module shown in FIG. 7.
Figure 11B:
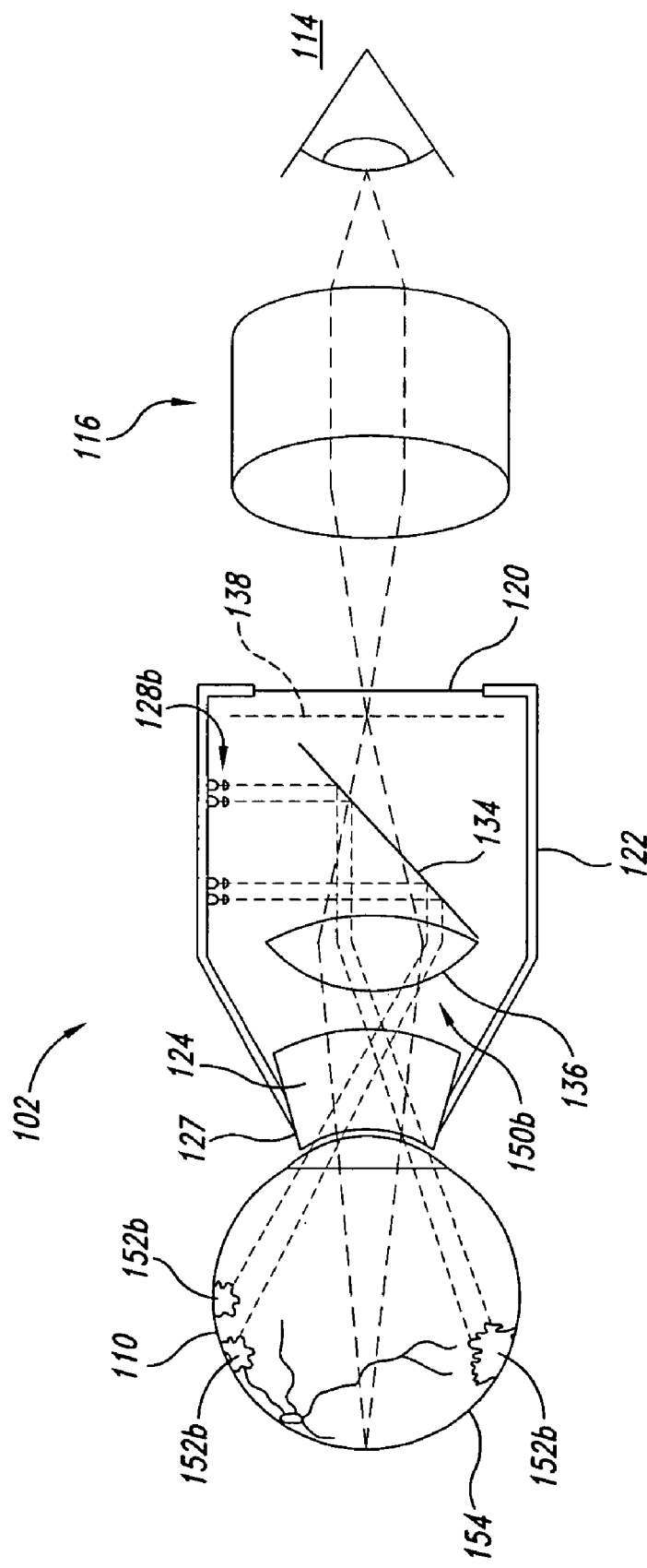
FIG. 11B is a cross-sectional schematic showing an optical raytrace of an alternative optical module for treating disease such as DR.
Figure 11C:
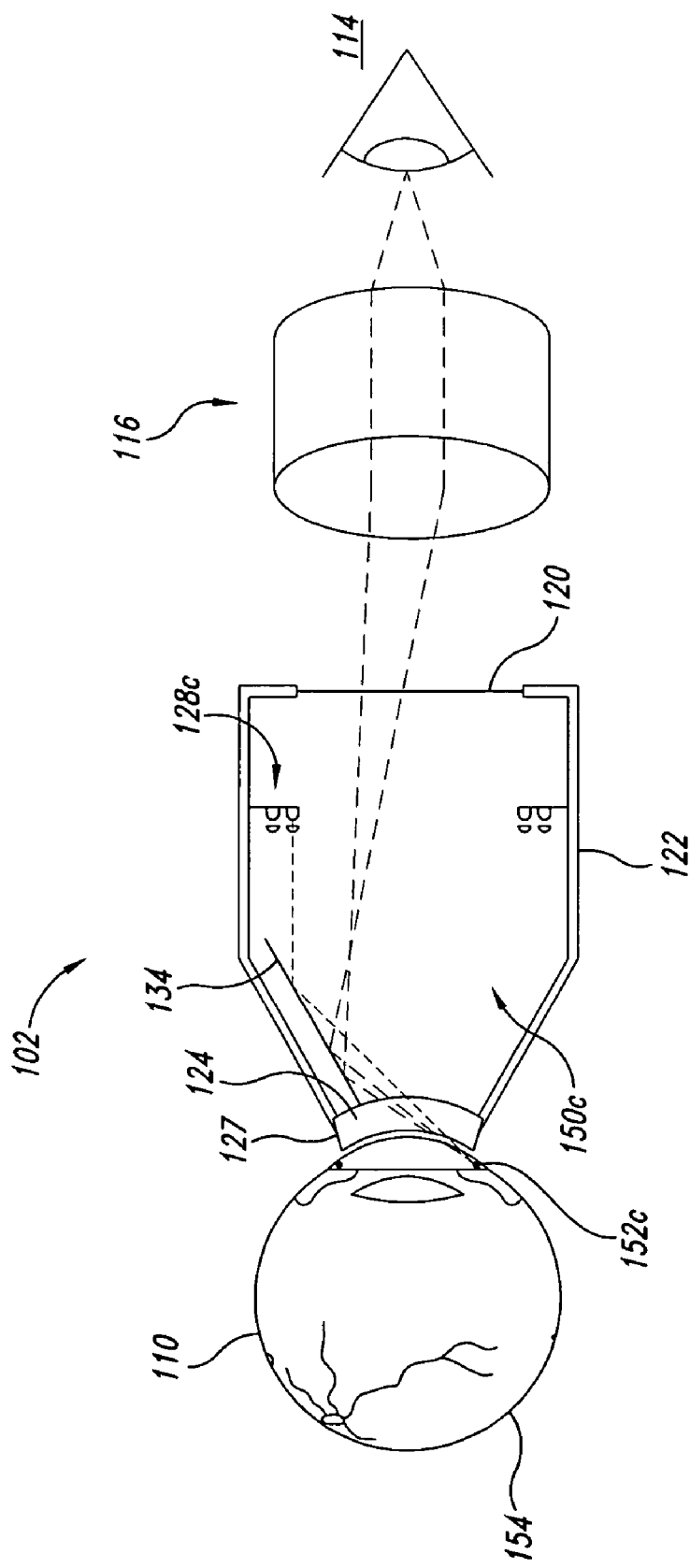
FIG. 11C is a cross-sectional schematic showing an optical raytrace of an alternative optical module for treating disease such as glaucoma.

An optical raytrace 150, depicted in FIG. 11A, shows coincident treatment illumination and visualization pathways allowing accurate aiming and exposure of therapeutic light to internal eye structures. Light is emitted from the illumination source 128 and strikes the selective reflector 134. The reflection spectrum portion of the illumination source light is reflected from the selective reflector 134 and passes through the lens 136 and the contact 124 to enter into the eye 110 to substantially strike targeted eye tissue 152. An alternative optical raytrace 150b, shown in FIG. 11B, depicts how light from an illumination source 128b associated with pattern 144b is directed to strike targeted eye tissue 152b associated with disease such as DR. Another alternative optical raytrace 150c, shown in FIG. 11C, depicts how light from an illumination source 128c associated with pattern 144c is directed to strike targeted eye tissue 152b such as trabecular mesh work of the eye 110 associated with disease such as glaucoma.

Figure 12A:
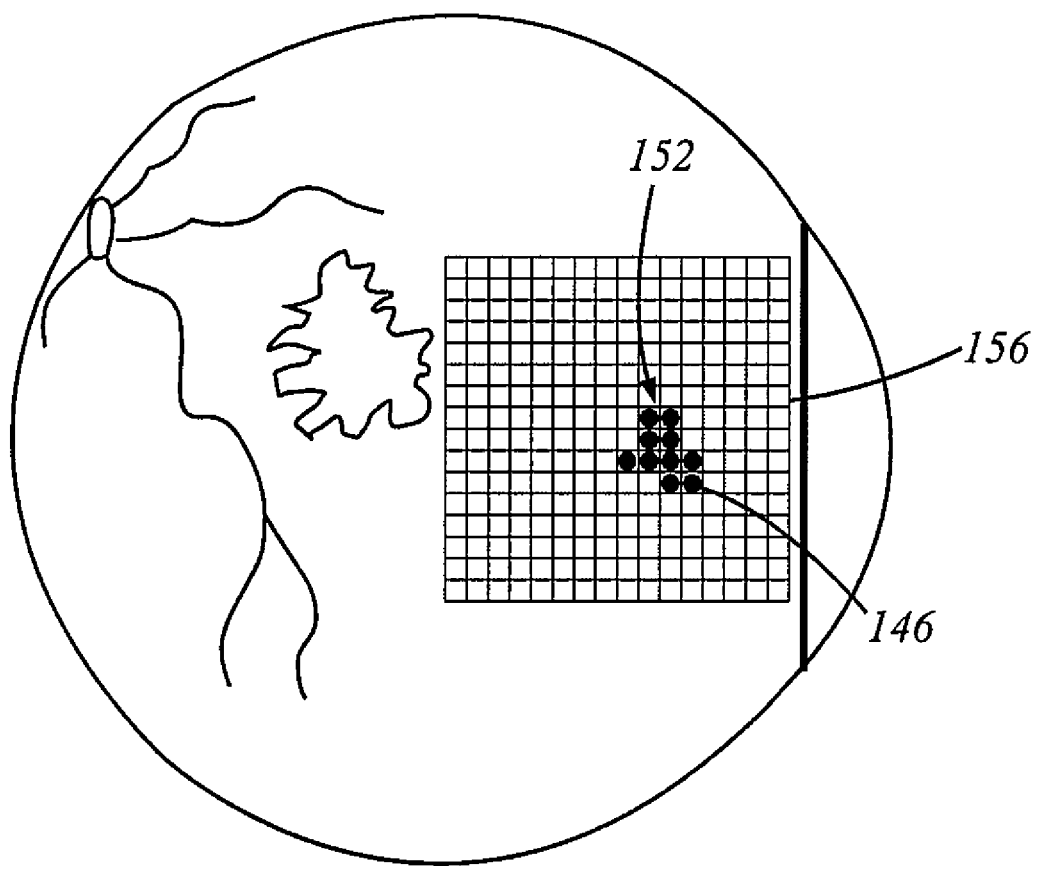
FIG. 12A is an exemplary image as seen through the microscope shown in FIG. 2.
Figure 12B:
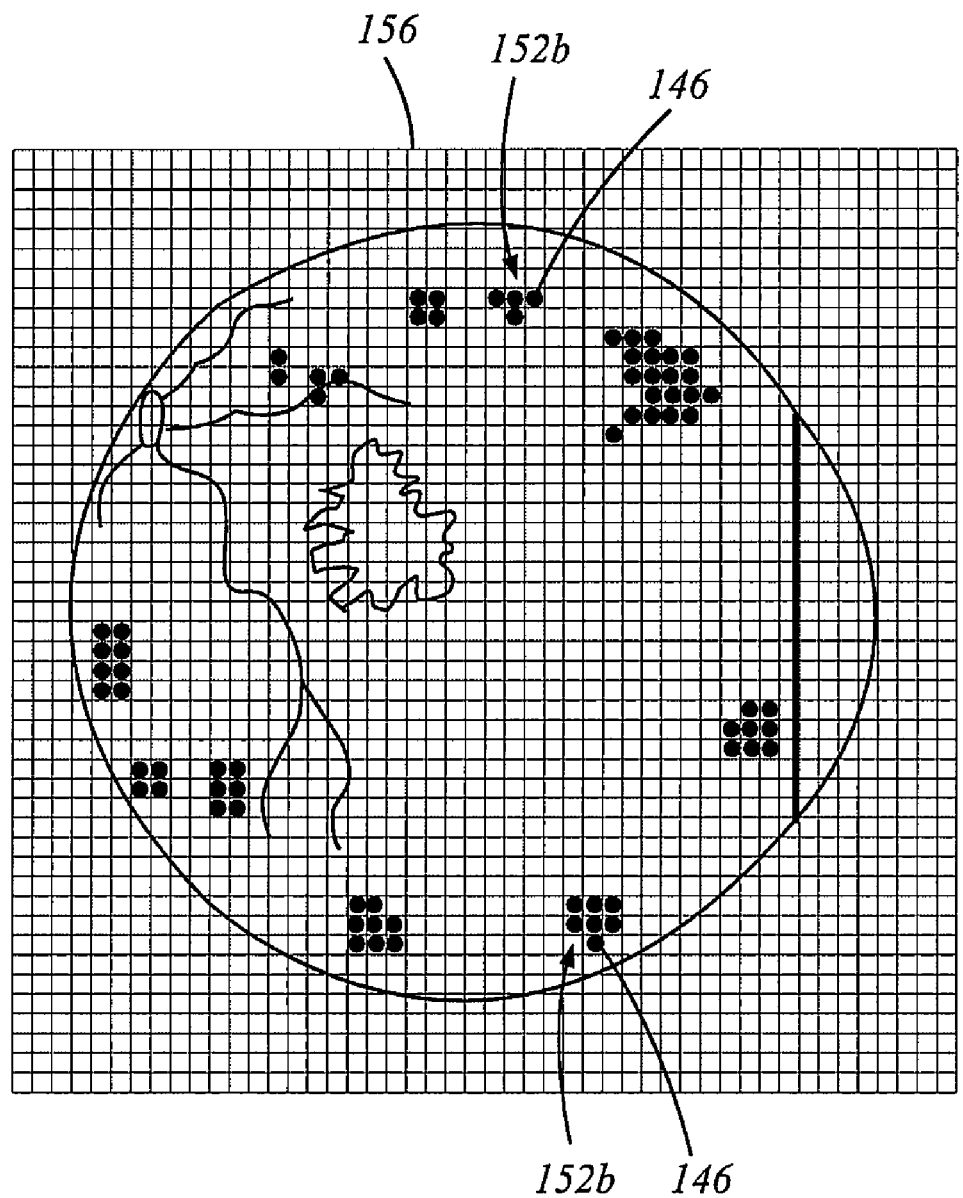
FIG. 12B is an alternative image as seen through the microscope associated with the alternative illumination pattern shown in FIG. 9B for treating disease such as DR.

Visualization illumination generated by the microscope 116 passes through the visualization interface 120 inside the housing 122. Some portions of the visualization illumination in the pass spectrum can pass through the selective reflector 134 to be subsequently reflected off of the eye 110 and back through the selective reflector to be collected by the microscope 116 for viewing detail of the eye by the clinician 114. Due to the drop in efficiency of the selective reflector 134 for portions of the reflection spectrum of the illumination source light farther from the activation wavelength, those portions partially pass through the selective reflector when they are reflected off of the targeted eye tissue 152 so that the clinician 114 can also see where the primary excitation illumination areas 146 are positioned as shown in the exemplary depiction of FIG. 12A. The targeted eye tissue 152 shown in the example of FIG. 12A has ten primary excitation illumination areas 146. Also shown in FIG. 12A is a grid pattern 156 that has been added for illustrative purposes to show which of the LEDs 130 of a 16×16 array of LEDs were lit. An example of the targeted eye tissue 152b has multiple illumination areas 146 peripherally placed for treatment of disease such as DR. In a targeting mode, implementations use power levels for the LEDs 130 to light the LEDs below intensity levels necessary to activate the photosensitizer of interest. The primary excitation illuminations areas 146 can then be viewed through the microscope 116 to aid in their selection and positioning. Once a determination is made as to which of the LEDs 130 are to be designated for use in treatment and how their primary excitation illumination areas 146 are to be positioned onto the targeted eye tissue 152, treatment can begin. During treatment, power is provided to the designated of the LEDs 130 to light the LEDs at intensity levels for the one or more activation wavelengths to active the photosensitizer of interest.

Figure 13:
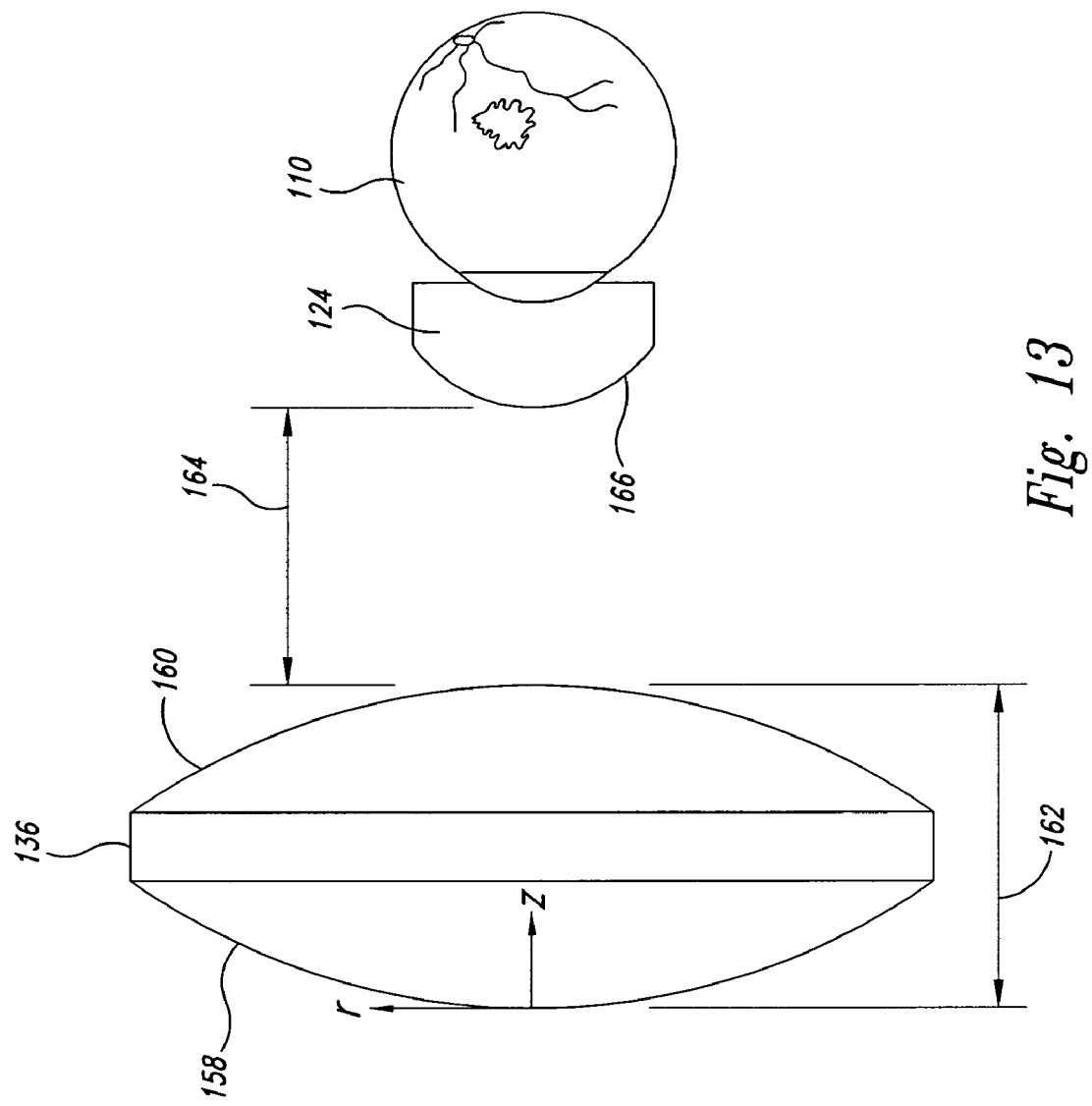
FIG. 13 is a cross-sectional representation of lenses used in the optical module shown in FIG. 7.

As shown in FIG. 13, the lens 136 has a posterior surface 158 and an anterior surface 160 so shaped to allow for its role in beam treatment and visualization. Implementations use configurations for the lens 136 according to the following formula: $z=1+cr^2(1-(1+k)c^2r^2)^{-1/2}+A_1r^2+A_2r^4+A_3r^6$ and $c^{-1}=R$, where for the posterior surface 158 the following values apply: $R=32\pm2$, $k=-0.98\pm0.5$, $A_1=2.37$ E$-4\pm0.2$, $A_2=-7$ E$-6\pm0.01$, $A_3=-7.76$ E$-10\pm0.001$, where r and z are in millimeters. For the anterior surface 160, the following values apply: $R=-27\pm2$, $k=-1.40\pm0.5$, $A_1=4$ E$-3\pm0.02$, $A_2=-9$ E$-6\pm0.01$, $A_3=-9.48$ E$-9\pm0.001$.

Under these implementations the lens 136 has a thickness 162 of approximately 15.5 mm and is positioned a distance 164 that is approximately 13.7 mm from the contact 124. In these implementations, the contact 124 has an anterior surface 166 that is substantially that of a spherical lens with substantially a 9 mm radius.

As shown in FIGS. 14 and 15, further implementations mount the selective reflector 134 onto a movable frame 170 that is movably coupled to the housing 122. In some implementations, the movable frame 170 comprises a receiving portion 172 to hold the selective reflector 134, a control portion 174 at an end of the frame that is accessible external to the housing 122, and a ball 176 rotatably coupled to a socket 178 located on another end of the frame coupled internal to the housing. In these implementations the movable frame can be adjusted to change the angles at which the parallel light 142 approaches and is reflected from the selective reflector 134 to position the primary excitation illumination areas 146 onto targeted eye tissue. The ability of repositioning the primary excitation illumination areas 146 through use of the movable frame 170 allows for use of a smaller array of the LEDs 130 if desired since a particular illumination shape can be formed by lighting a selected number of the LEDs and then the particular illumination shape can be moved into position to strike targeted eye tissue. As discussed above, with a larger array of LEDs, generating and positioning an illumination shape can be done through LED selection without need of changing reflection angles of the parallel light 142 from the selective reflector 134.

Figure 16:
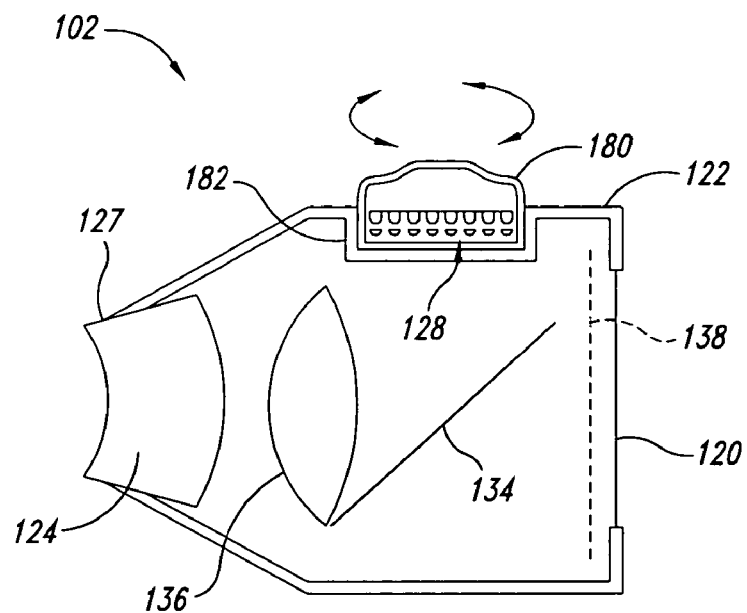
FIG. 16 is a cross-sectional schematic of an implementation of the optical module including rotatable coupling of the illumination source to the housing of the optical module.
Figure 17:
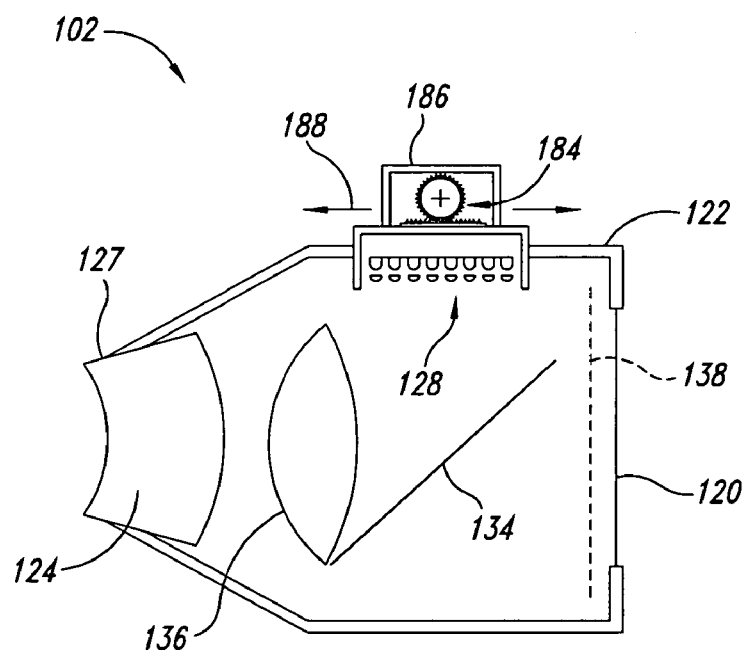
FIG. 17 is cross-sectional schematic of an implementation of the optical module including slidable coupling of the illumination source to the housing of the optical module.

Other implementations movably couple the illumination source 128 to the housing 122. The implementation shown in FIG. 16 locates the illumination source 128 inside of an enclosure 180 that is positioned inside of a channel 182 to rotatably couple the illumination source to the housing 122. In another implementation shown in FIG. 17, a rack gear arrangement 184 is used to slideably engage an enclosure 186 containing the illumination source 128 so that the illumination source is repositioned along the direction of arrows 188. By moving the illumination source with respect to the selective reflector 134, a smaller sized array of the LEDs 130 can be used with similar results as those discussed above with respect to the movable frame 170.

Figure 18:
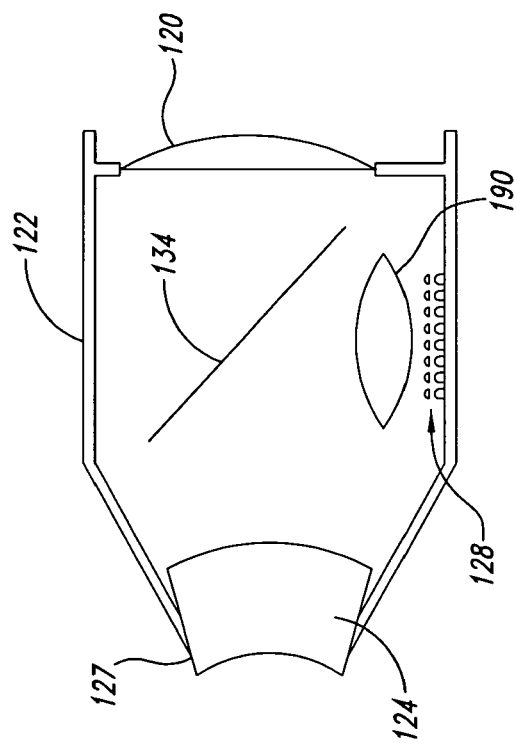
FIG. 18 is a cross-sectional schematic of another implementation of the optical module using separate lenses for beam treatment and visualization portions of the optical module.
Figure 19:
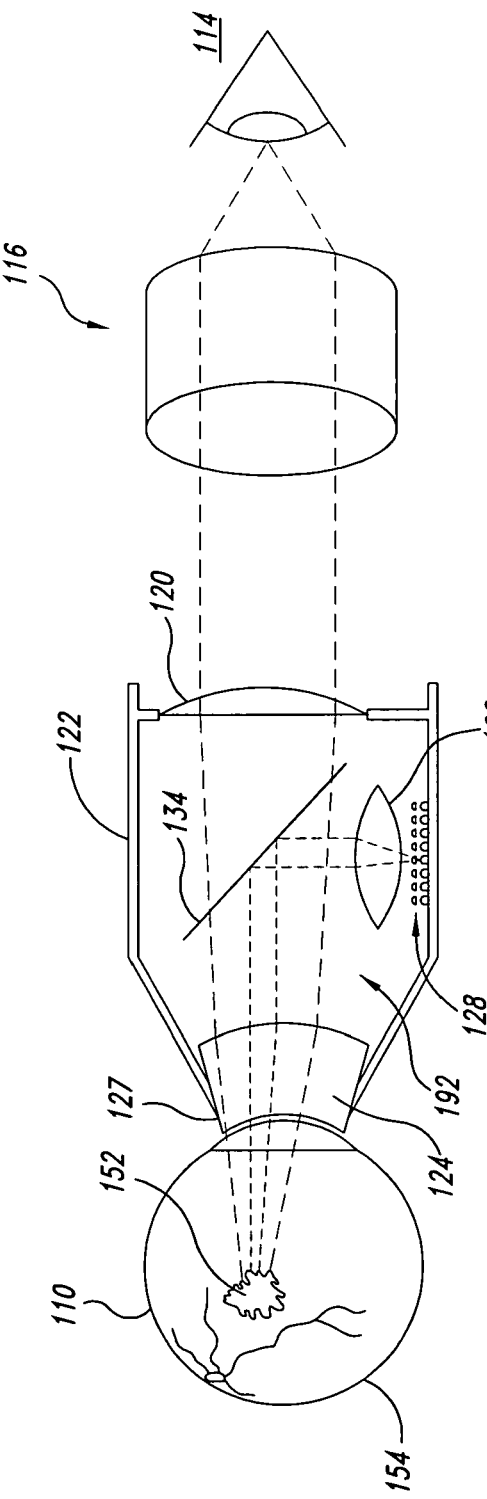
FIG. 19 is a cross-sectional schematic of the optical module shown in FIG. 18 including an optical raytrace.

Some implementations assign the beam treatment and visualization roles to separate lenses. For instance, the implementation shown in FIG. 18 uses a lens 190 that is positioned between the illumination source 128 and the selective reflector 134 so that the lens 190 focuses the parallel light 142 from the illumination source 128 to be reflected onto the targeted eye tissue 152. As to the visualization role, the visualization interface 120 includes a focusing lens to focus light from the eye 110 to be viewed through the microscope 116 as shown in an optical raytrace 192 of FIG. 19.

Figure 20:
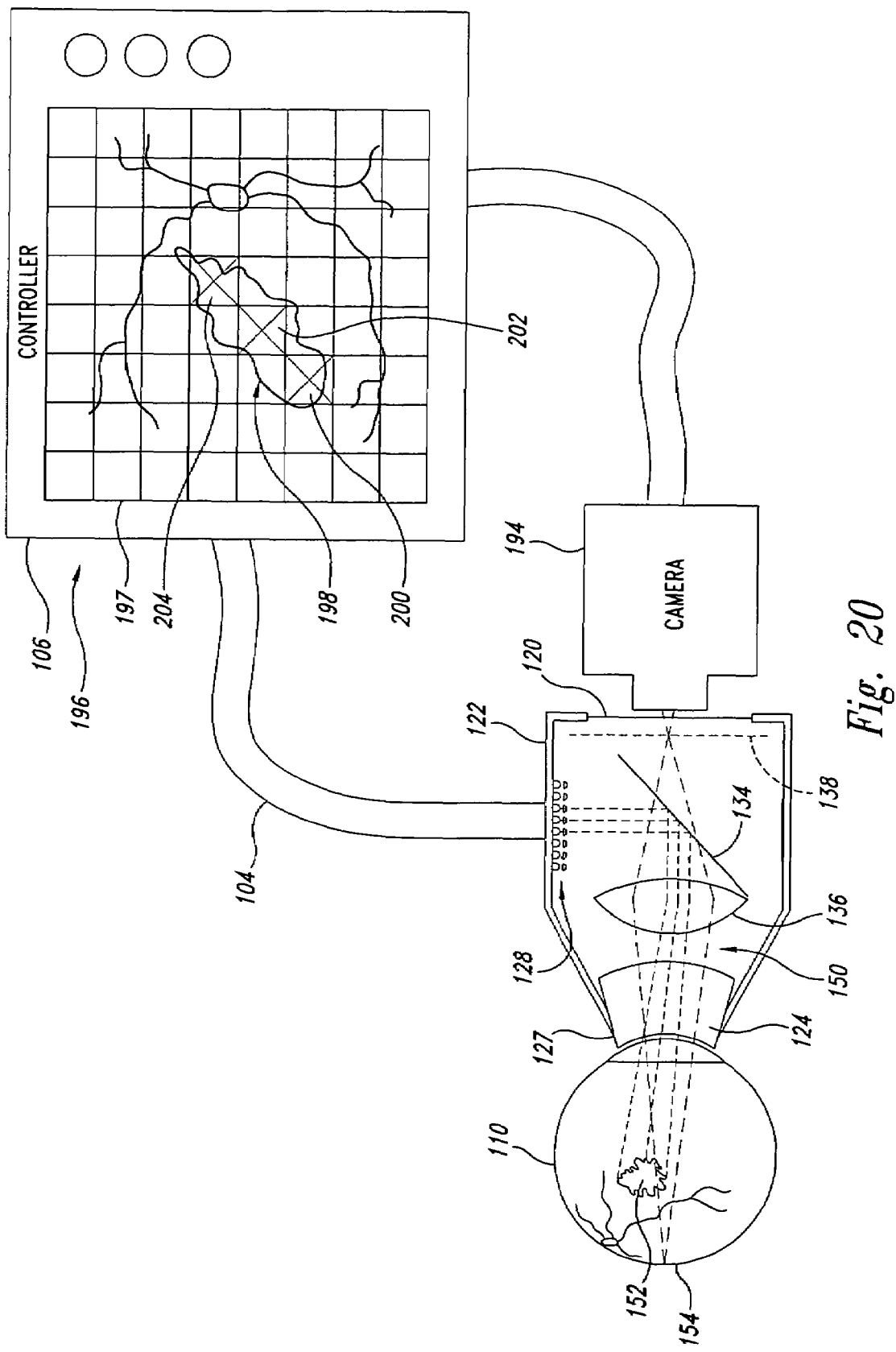
FIG. 20 is a cross-sectional schematic of an implementation of the optical module interfaced to a video camera used for an implementation of the controller having a touchscreen.

The visualization interface 120 is used in other implementations to provide viewing access to the eye 110 for camera equipment such as the video camera 194 coupled to the controller 106 shown in FIG. 20. In this implementation, the controller 106 includes a touch screen 196 with a grid 197 to touch select which of the LEDs 130 are activated. The controller 106 receives a video image of the rear portion 154 of the eye 110 from the camera 194 and overlays the image onto the grid 197. Alignment of the grid 197 with the video image can be accomplished by activating at a targeting intensity two pre-designated LEDs having known locations with respect to their array. The resultant primary excitation illumination areas 146 will then be displayed on the video image so that the grid 197 or primary excitation illumination areas can be moved to coincide with each other on the touch screen 196. As shown in FIG. 20, diseased eye tissue has been identified as targeted eye tissue 152 on the touch screen 196 by use of "X" marks in squares 200, 202, and 204 of the grid .197.

The foregoing described embodiments depict different components contained within, or connected with, different other components. It is to be understood that such depicted configurations are merely exemplary, and that other configurations can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of configurations or intermedial components. Likewise, any two components so associated can also be viewed as being "operably connected", or "operably coupled", to each other to achieve the desired functionality. While particular embodiments of the present invention have been shown and described, it will be obvious to those skilled in the art that, based upon the teachings herein, changes and modifications may be made without departing from this invention and its broader aspects.

We claim:

1. A system for illuminating a target area of an eye treated with a photosensitizer, the system comprising:

a contact portion configured to interface with the eye to provide an optical path between the eye and the system;

a plurality of light emitters configured to emit light having an emissions spectrum with at least an activation wavelength of the photosensitizer;

a selective reflector configured to reflect at least a majority of light having the activation wavelength of the photosensitizer and to pass at least some light having wavelengths other than the activation wavelength, the selective reflector positioned to receive emitter light and to direct a portion of the emitter light reflected from the selective reflector toward the contact portion, the selective reflector positioned to receive and pass a portion of light reflected from the eye and passed by the contact portion; and a visualization portion positioned to receive and pass that portion of light reflected from the eye and passed by the selective reflector, wherein each of the light emitters has a light source and includes a lens having a focal length and being spaced from the light source of the light emitter by substantially the focal length of the lens.

2. A system for illuminating a target area of an eye treated with a photosensitizer, the system comprising:

a contact portion configured to interface with the eye to provide an optical path between the eye and the system;

a plurality of light emitters configured to emit light having an emissions spectrum with at least an activation wavelength of the photo sensitizer;

a selective reflector configured to reflect at least a majority of light having the activation wavelength of the photosensitizer and to pass at least some light having wavelengths other than the activation wavelength, the selective reflector positioned to receive emitter light and to direct a portion of the emitter light reflected from the selective reflector toward the contact portion, the selective reflector positioned to receive and pass a portion of light reflected from the eye and passed by the contact portion; and a visualization portion positioned to receive and pass that portion of light reflected from the eye and passed by the selective reflector, wherein the contact portion is rotatably coupled to another portion of the system to manipulate intensity of the emitter light received by the target area of the eye.

3. A system for illuminating a target area of an eye, the system comprising:

a plurality of light emitters;

a selective reflector positioned to receive emitter light and to direct a portion of the emitter light to be received by the eye, the selective reflector positioned to receive and pass a portion of light reflected from the eye;

an electronic image capture device positioned to receive as an image a portion of the light passed by the selective reflector;

a controller electrically coupled to the plurality of light emitters to selectively activate ones of the light emitters;

an electronic monitor electrically coupled to the electronic image capture device to display images captured by the electronic image capture device; and a touch screen device overlayed onto the electronic monitor, the touch screen device electrically coupled to the controller to select activation of the light emitters.

4. A system for illuminating a target area of an eye, the system comprising:

a plurality of light emitters; and a selective reflector positioned to receive emitter light and to direct a portion of the emitter light to be received by the eye, the selective reflector positioned to receive and pass a portion of light reflected from the eye;

wherein the selective reflector is movably mounted such that position of the selective reflector with respect to the plurality of light emitters is adjustable.

5. The system of claim 4 wherein the selective reflector is movably mounted through a pivotal coupling.

* * * * *